United States Patent [19]

Nicolas

[11] Patent Number: 5,308,858
[45] Date of Patent: May 3, 1994

[54] USE OF ADDITIVES FOR PRESERVATIVE CARRIER OILS TO IMPROVE THEIR EFFICACY AGAINST WOOD DECAY

[75] Inventor: Darrell D. Nicolas, Starkville, Miss.

[73] Assignee: Electric Power Research Institute, Palo Alto, Calif.

[21] Appl. No.: 803,138

[22] Filed: Dec. 5, 1991

[51] Int. Cl.$^5$ ............................................. A01N 43/80
[52] U.S. Cl. .................................................... 514/372
[58] Field of Search .......................................... 514/372

[56] References Cited

U.S. PATENT DOCUMENTS

| | | | |
|---|---|---|---|
| 4,322,475 | 3/1982 | Lewis et al. | 514/372 |
| 4,325,201 | 4/1982 | Lewis et al. | 47/57.6 |
| 4,454,146 | 6/1984 | Borovian | 424/270 |
| 4,822,511 | 4/1989 | Law | 252/106 |
| 4,869,934 | 9/1989 | Jethwa | 427/393.5 |
| 4,964,892 | 10/1990 | Hsu | 514/372 |
| 4,980,176 | 12/1990 | Berke et al. | 424/682 |

FOREIGN PATENT DOCUMENTS

| | | | |
|---|---|---|---|
| 0174086 | 3/1986 | European Pat. Off. | 514/372 |
| 2171601 | 9/1986 | United Kingdom | 514/372 |

*Primary Examiner*—Allen J. Robinson
*Attorney, Agent, or Firm*—Flehr, Hohbach, Test, Albritton & Herbert

[57] ABSTRACT

This invention describes novel compositions for the treatment of wood. Specifically, compositions containing isothiazolones in petroleum and solvent carriers containing vinsol are produced to treat wood for protection against bacteria and fungi.

10 Claims, 4 Drawing Sheets

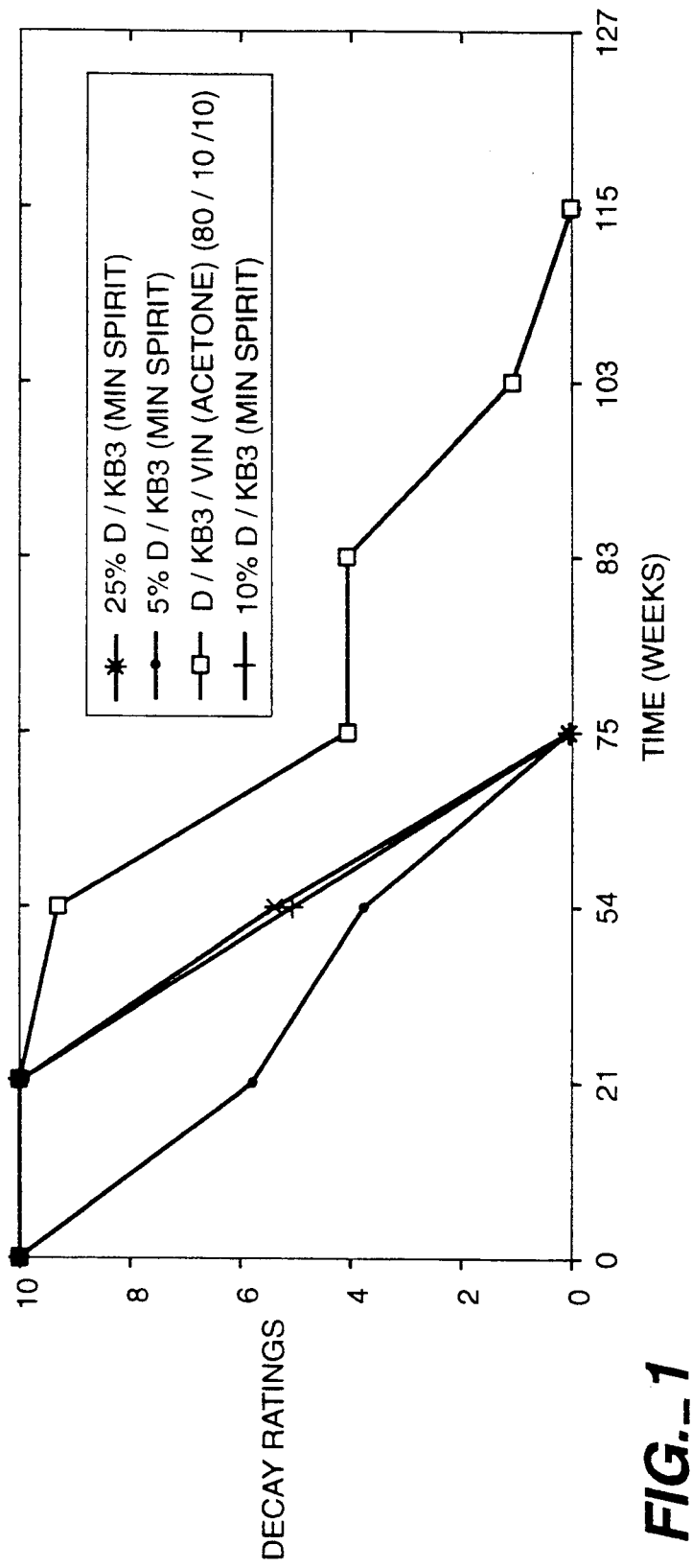
FIG._1

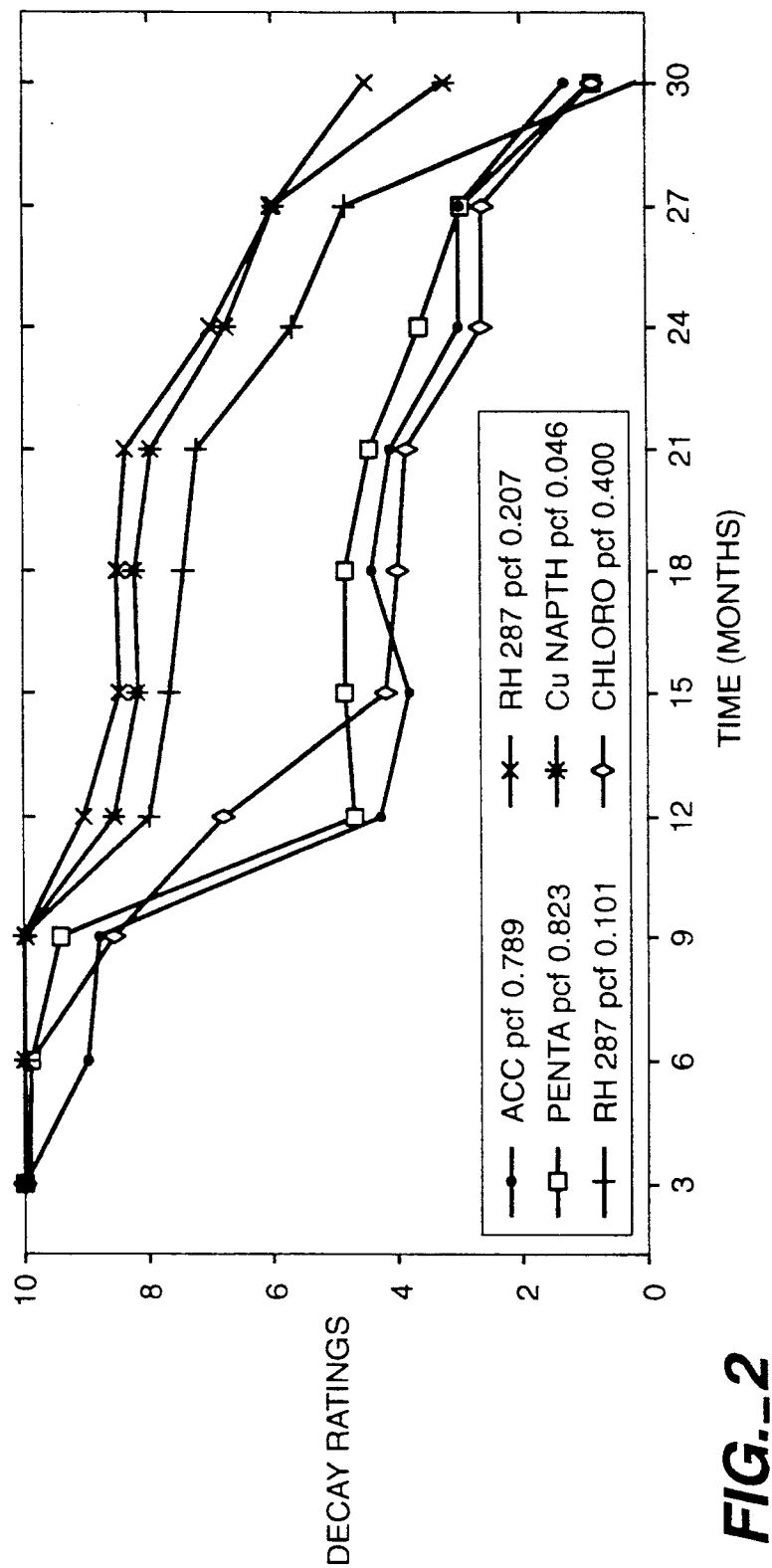
FIG._2

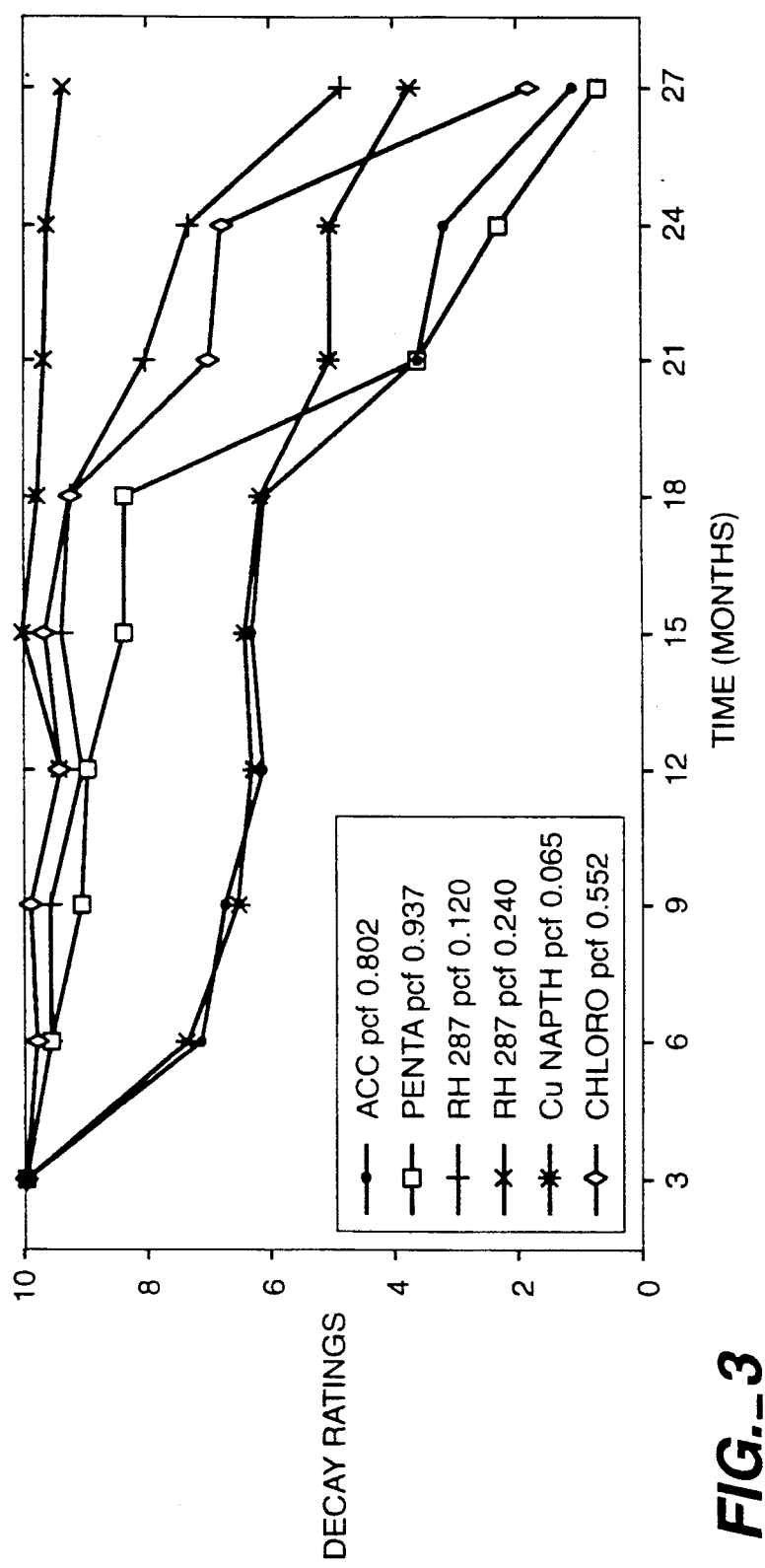
FIG._3

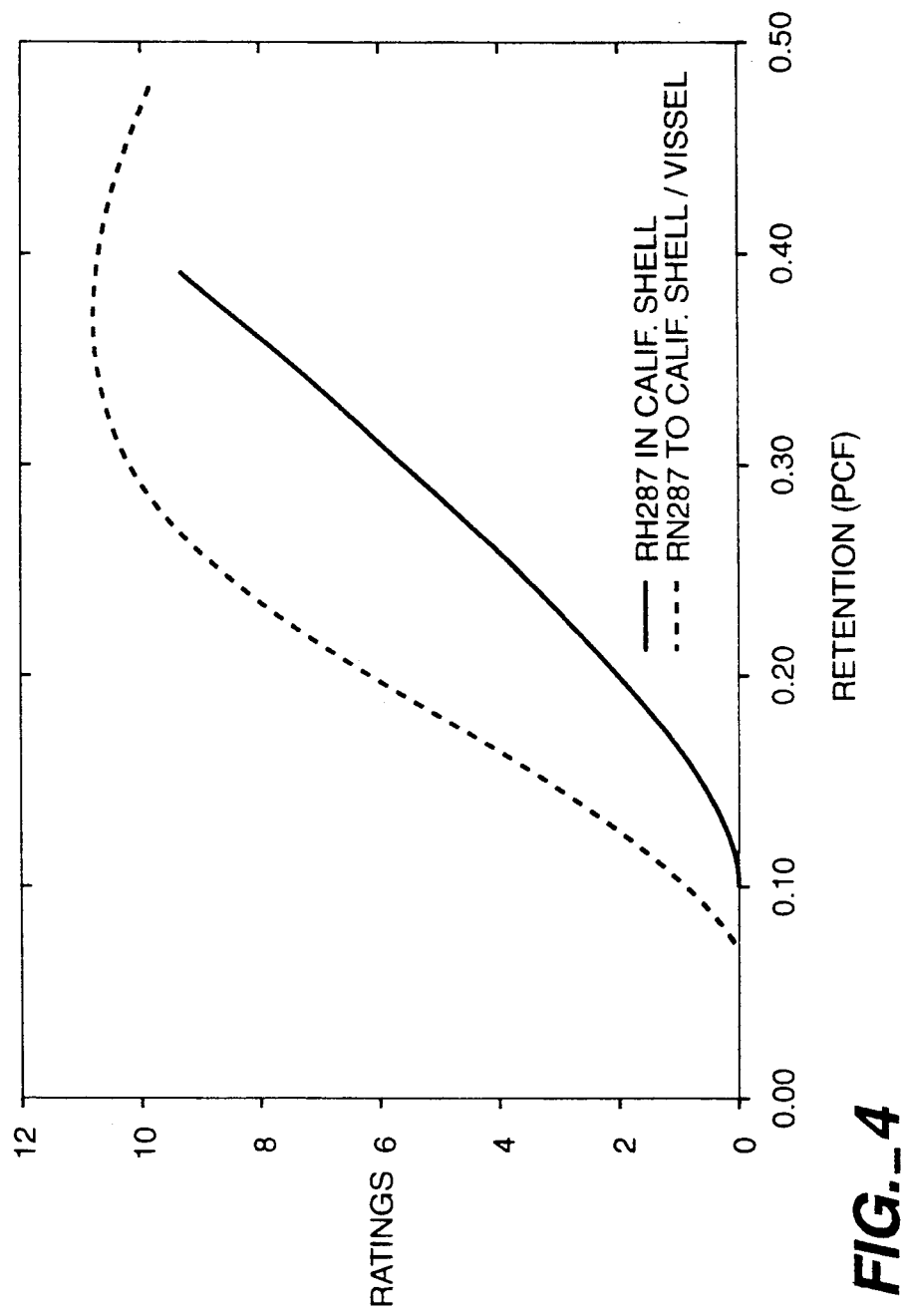
FIG._4

5,308,858

USE OF ADDITIVES FOR PRESERVATIVE CARRIER OILS TO IMPROVE THEIR EFFICACY AGAINST WOOD DECAY

FIELD OF THE INVENTION

This invention involves preservative and treatment substances for wood, specifically anti-bacterial and anti-fungal preparations in petroleum and solvent carriers.

BACKGROUND OF THE INVENTION

When exposed to the natural environment, wood supports, such as telephone poles, railroad ties, fence posts and the like, are prone to a variety of degradative effects. Particularly with wood supports maintained at or below ground level, a variety of bacterial and fungal pests contribute to the rapid deterioration of the wood.

A wide spectrum of wood treatment and preservative compositions are known. Creosotes, oils, paint additives, bacteriostats and fungistats have been used to block the action of the elements and the pests. Currently used compositions have varied effectiveness and the costs associated with their usage are a factor in their utility. However, it would be useful to have a cost-effective bacteriostatic and fungistatic treatment and preservative in an easy to apply composition.

The wood treatment and preservative compositions of this invention exhibit these desirable properties. Widely available components are combined in this invention to produce a surprisingly effective synergistic effect for treatment and protection of wood.

DESCRIPTION OF THE FIGURES

FIG. 1 shows the decay ratings of wood treated with diesel/KB-3 (No. 2 diesel fuel; solvent KB-3, CAS Reg. No. 68990-20-5; Eastman Chemical Products, Kingsport, Tenn.) and diesel/KB-3/Vinsol when tested by exposure to a fungus cellar for periods of over two years. The test results are rated according to the field stake standard M7-90 rating system of the American Wood Preservatives Association (AWPA Standard). The scale of this test is from 0 to 10, a 10 rating given to wood showing no degradation, and a rating of 0 is assigned to wood showing complete degradation. The graph shows the advantage of wood treatment with the treatment composition diesel/KB-3/Vinsol/acetone, at 50% weight/weight (w/w) diesel, 10% w/w KB-3, and 10% w/w Vinsol, 30% weight/weight (w/w) acetone.

FIG. 2 uses the same decay rating system as FIG. 1 to show the advantage of treatment compositions containing isothiazolones (4,5-dichloro-2-N-octyl-4-isothiazolone-3-one="RH 287") at various concentrations in a Shell Oil P9-A/toluene carrier solution at approximately 20% w/w P9-A to 80% w/w toluene.

FIG. 3 shows the unexpected advantage of treatment compositions containing an isothiazolone (RH 287 here) in combination with Vinsol. The treatment composition in this figure is Shell Oil P9-A/Vinsol/acetone/toluene at 20/2.5/40/37.5% w/w. The solution containing 1.0% RH287 resulted in a retention of 0.240 pounds per cubic foot (pcf) in wood which showed surprising resistance to decay throughout the two year test period, when compared to the other compositions.

FIG. 4 shows a dose-response curve for wood treated with the isothiazolone RH 287 in carriers with and without the addition of Vinsol. The same rating system is used. The abscissa charts the retention of the isothiazolone in the wood being tested, in units of pcf. The figure shows the advantage of treatment of wood with isothiazolone in a treatment composition containing Vinsol and one or a mixture of commonly used solvent.

DETAILED DESCRIPTION OF THE INVENTION

According to the invention, Vinsol (a residue of solvent extraction of pine stumps, which is typically used to produce resin acids, resins, and the like; this product is sold as "Vinsol", Hercules, Inc.) and at least one isothiazolone are mixed in a hydrocarbon carrier to produce a composition for the protection and preservation of wood. Isothiazolone is one of a number of biocides, having both fungicidal and insecticidal properties.

Compositions of this invention may be prepared by, for example, adding one or more isothiazolones to a carrier containing petroleum products (diesel fuel, P9-A oil and the like), selected by-products of organic intermediates production, for example ketone production, such as KB-3 (KB=ketone bottom) and Vinsol. A wide range of compositions containing various amounts of these components may be effective.

Compositions of this invention may contain a variety of isothiazolones, alone or in combinations of one or more per composition. Preferred isothiazolones of this invention are Kathon 886F (a mixture containing 8.6% w/w 5-chloro-2-methyl-4-isothiazolone-3-one and 2.6% w/w 2-methyl-4-isothiazolone-3-one; [CAS Reg. No. 2682-20-4]), Skane M-8 (a mixture containing 2-n-octyl-4-isothiazolone-3-one; [CAS Reg. No. 26530-20-1]), and the like. The present preferred isothiazolone is 4,5-dichloro-2-N-octyl-4-isothiazolone-3-one. Suitably, the amount of isothiazolone in the treatment composition is in the range from about 0.05% w/w to about 2% w/w, preferably in the range from about 0.1–1.0% w/w.

Carriers of this invention contain petroleum products, alone or in combination with Vinsol solvents. Presently preferred carriers are those containing petroleum products such as Shell Oil (meeting the AWPA standard P9-A), diesel fuel (such as No. 2 diesel fuel) and the like. Suitably, petroleum products will be present in the treatment compositions in a range from about 10–95% w/w, preferably about 20% w/w.

Vinsol solvents of this invention will be non-aqueous organic solvents capable of efficiently solubilizing Vinsol. Thus, Vinsol solvents such as acetone, toluene, KB3 and the like are preferred, as are others well known to those skilled in the art. ("KB-3", Eastman Chemical Products, Inc., Kingsport, Tenn.) Suitably, the amount of Vinsol solvent in the treatment composition is in the range from about 5–90% w/w, preferably in the range from about 10–40% w/w.

In the presently preferred embodiment, the carrier is Shell Oil P9-A/acetone/toluene in a composition of approximately 20/40/40%/w/w of the components.

The relative portions of the components in these treatment compositions may be changed. For example, the portion of Vinsol in a carrier may be increased to about 40% w/w in certain carriers to produce treatment composition useful for the practice of this invention. Suitably, Vinsol is present in the treatment composition in a range from about 1–40% w/w, and preferably about 5–20% w/w.

Thus, in a preferred composition the range of isothiazolone is from about 0.1% w/w to about 2% w/w, the range of Vinsol is from about 1% w/w to about 40% w/w, the range of petroleum product is from about 10% w/w to about 95% w/w, and the range of Vinsol solvent is from about 90% w/w to about 5% w/w.

Compositions of this invention may be applied to the wood to be treated using a variety of well known processes such as dipping, spraying, painting and the like. The presently preferred method of application is by pressure treatment.

To better describe the compositions of this invention, the following example is provided, which is not intended to in any way limit the scope of the invention.

EXAMPLE

Isothiazolone 4,5-dichloro-2-N-octyl-4-isothiazolone-3-one (available as "RH 287", Rohm and Haas Industries, Philadelphia, Pa.) was added in concentrations from 0.5% w/w to 1% w/w to a treatment solution containing Shell Oil P9-A/Vinsol/acetone/toluene in a composition of approximately 20/2.5/40/37.5% w/w. This resulted in retention in wood of from about 0.120 pounds per cubic foot (pcf) to about 0.240 pcf of RH 287.

What is claimed is:

1. A composition for treatment and preservation of wood comprising Vinsol and a fungicidally or bactericidally effective amount of an isothiazolone in an inert carrier, said isothiazolone being selected from the group consisting of 4,5-dichloro-2-N-octyl-4-isothiazolone-3-one, 2-n-octyl-4-isothiazolone-3-one, and a mixture of 5-chloro-2-methyl-4-isothiazolone-3-one and 2-methyl-4-isothiazolone-3-one.

2. The composition of claim 1, wherein the amount of isothiazolone is from about 0.1% w/w to about 2% w/w.

3. The composition of claim 1, wherein the amount of Vinsol is about 1% w/w to about 40% w/w.

4. The composition of claim 1, wherein said isothiazolone is 4,5-dichloro-2-N-octyl-4-isothiazolone-3-one.

5. The composition of claim 1, wherein said carrier comprises a Vinsol solvent.

6. The composition of claim 5, wherein said Vinsol solvent is selected from the group consisting of KB-3, acetone and toluene.

7. A method for preventing degradation of wood by bacteria and fungi which comprises treating said wood with a fungicidally bactericidally effective amount of the composition of claim 1.

8. The composition of claim 1 wherein the amount of isothiazolone is from 0.1% w/w to about 2% w/w and the amount of Vinsol is about 1% w/w to about 40% w/w.

9. A method for preventing degradation of wood by bacteria and fungi which comprises treating said wood with a fungicidally and bactericidally effective amount of the composition of claim 2.

10. A method for preventing degradation of wood by bacteria and fungi which comprises treating said wood with a fungicidally and bactericidally effective amount of the composition of claim 3.

* * * * *

UNITED STATES PATENT AND TRADEMARK OFFICE
CERTIFICATE OF CORRECTION

PATENT NO. : 5,308,858
DATED : May 3, 1994
INVENTOR(S) : Darrell D. Nicholas

It is certified that error appears in the above-indentified patent and that said Letters Patent is hereby corrected as shown below:

On the Title page, items [19] and [54], inventor: delete "Nicolas" and insert --Nicholas--.

Signed and Sealed this

Thirtieth Day of August, 1994

Attest:

BRUCE LEHMAN

Attesting Officer

Commissioner of Patents and Trademarks